Figure 1:
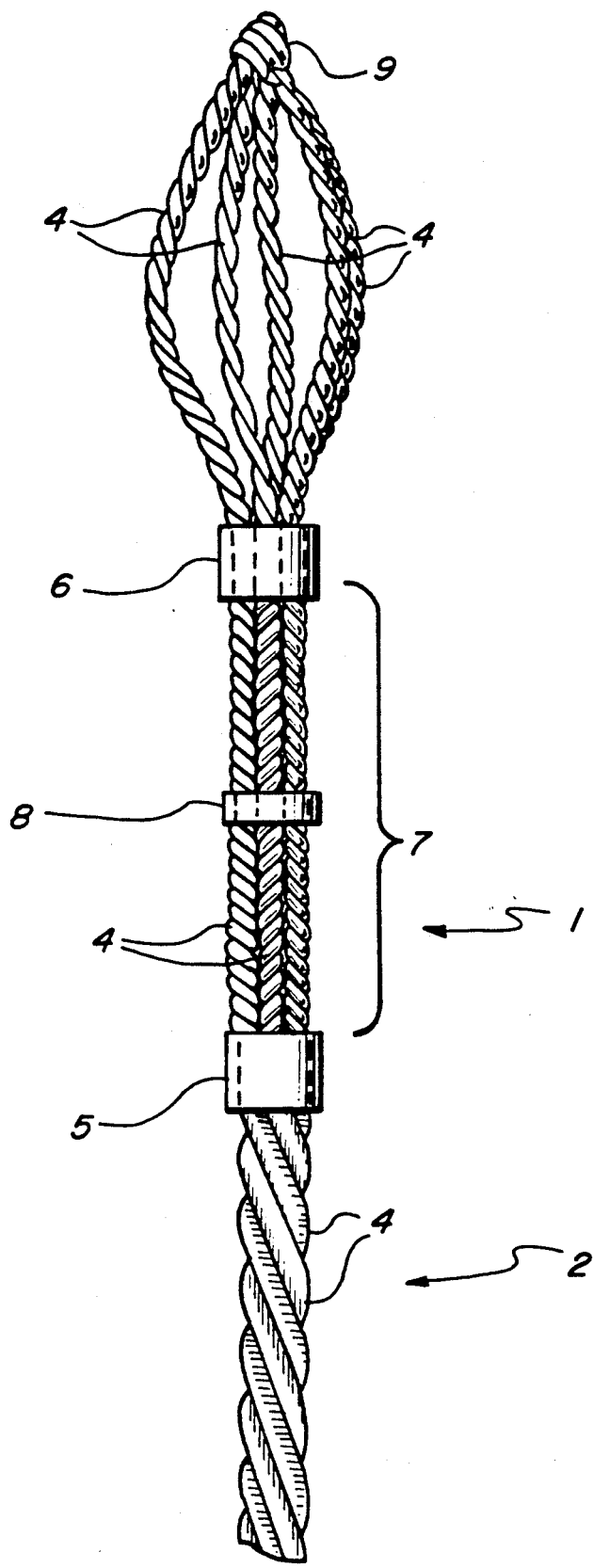

United States Patent [19]
Wechler

[11] Patent Number: 5,098,441
[45] Date of Patent: Mar. 24, 1992

[54] LITHOTRIPTOR

[75] Inventor: Ingolf M. Wechler, Grabenstätt, Fed. Rep. of Germany

[73] Assignee: Dr. Andreas Lindner Unternehmensberatung, Munich, Fed. Rep. of Germany

[21] Appl. No.: 504,873

[22] Filed: Apr. 5, 1990

[30] Foreign Application Priority Data

Apr. 5, 1989 [DE] Fed. Rep. of Germany ... 8904212[U]
Apr. 5, 1989 [DE] Fed. Rep. of Germany ... 8904213[U]

[51] Int. Cl.⁵ .............................................. A61B 17/22
[52] U.S. Cl. ................................................... 606/113
[58] Field of Search ........................ 606/113, 127, 128

[56] References Cited

U.S. PATENT DOCUMENTS

| | | | |
|---|---|---|---|
| 1,612,697 | 12/1926 | Cecil | 606/127 |
| 2,918,919 | 12/1959 | Wallace | 606/127 |
| 3,108,594 | 10/1963 | Glassman | 606/127 |
| 4,046,150 | 9/1977 | Schwartz et al. | 606/127 |
| 4,486,680 | 12/1984 | Bonnet et al. | 606/128 |
| 4,682,599 | 7/1987 | Konomura | 606/127 |
| 4,741,335 | 5/1988 | Okada | 606/127 |

FOREIGN PATENT DOCUMENTS 3521717 12/1985 Fed. Rep. of Germany ...... 606/127

Primary Examiner—Michael H. Thaler
Attorney, Agent, or Firm—Price, Gess & Ubell

[57] ABSTRACT

Lithotriptor with a catch basket which is formed by a plurality of outwardly curved catch strings made of wire material and which comprises a catch basket foot and a catch basket top to which the catch strings are fixed to each other, the catch strings being connected at the catch basket foot to a pull string which consists of a plurality of pull wires and which is guided in a casing, the pull string being slidably arranged in the casing by means of a pull mechanism for introducing and retracting the catch basket. For achieving a large load transmission the pull string is formed by a wire rope being stranded at least twice, the number of strands of which corresponds to at least the number of catch strings of the catch basket, wherein the catch strings are formed by deformed rope strands of the wire rope which continuously run from the wire rope up to the top of the catch basket.

12 Claims, 3 Drawing Sheets

LITHOTRIPTOR

The invention is related to a lithotriptor with a catch basket which is formed by a plurality of outwardly curved catch strings made of wire material and which comprises a catch basket foot and a catch basket top at which the catch strings are fixed to each other, the catch strings being connected at the catch basket foot to a pull string which consists of a plurality of pull wires and which is guided in a casing, the pull string being slidably arranged in the casing by means of a pull mechanism for introducing and retracting the catch basket.

A conventional lithotriptor is for instance known from the German utility model 87 06 587. There an endoscopic lithotriptor is described having a flexible catheter as casing, into the distal end of which a catch basket being formed of a plurality of catch wires is retractable by means of a pull string which is connected to the pull wires and led through the catheter. The pull string is fixed to a pull rod which is axially slidable within a handle to which the catheter is connected. The pull rod is provided with an outside thread which engages into an adjusting screw nut supportable by the handle. Such a lithotriptor is introduced through an instrument channel of an endoscope into a body channel and serves to destroy larger stones and other larger concrements within the body of the patient. Hereby the catheter is introduced via the instrument channel of the endoscope with the catch basket being retracted into the distal end of the catheter, until this end leaves the instrument channel of the endoscope. Then the pull rod is slided in the handle whereby the catch basket leaves the distal end of the catheter and unfolds due to the deformation of the catch wires. After the concrement is captured in the catch basket the catch basket is retracted into the catheter due to drawing the pull rod out of the handle to such an extent that the catch wires tightly enclose the concrement. Thereafter the adjusting screw nut is screwed on the outside thread of the pull rod up to striking against the related frontal end of the handle. Then, due to further turning the adjusting screw nut, the catch wires of the catch basket are further retracted into the distal end of the catheter with a relatively large force which is generated due to the multiplication of the thread. The catch wires are cut into the concrement and decompose it. For the decomposition of hard concrements it is often necessary to transfer considerable forces to the catch basket. For that reason the pull string has to have a correspondingly high tensile strength. Further, the pull string has to be fixed sufficiently tight in the clamping device and must not be weakened in its strength by the clamping device itself. At the known lithotriptor the clamping of the pull string takes place by means of a clamping screw which may lead to a damage of the pull string if a large lateral clamping pressure occurs.

Another lithotriptor is known from the German utility model 86 26 048. There the catch basket is formed by three endless loop-shaped catch strings each one being formed by a plurality of plaited or spined single wires. Due to the manufacturing of the catch strings using respectively a plurality of plaited or spined single wires the tensile strength of each catch string is increased, however, these catch strings end without interruption into the pull string at the foot of the catch basket, the pull string thus being formed by a plurality of parallel single strings which continuously pass to the end of the device at the operator side. Such a pull string made of a plurality of single strings, however, leads to problems regarding the fixing of the pull string in the handle of the lithotriptor at the operator side or, respectively, in the pull mechanism formed in the handle for pulling the pull string, and to problems regarding the distribution of the forces over the single strings. So it may happen that, during the attempt to decompose an extremely hard concrement captured in the catch basket, a part of the single strings is overloaded and ruptures which as a consequence may lead to a rupture of the other single strings also, so that the catch basket and the ruptured string parts can only be removed by an operation. Further, this known lithotriptor involves the danger that the catch basket cannot be detached from an extremely hard and therewith indestructible concrement and the concrement is too large as to be retractable with the catch basket through the instrument channel of the endoscope. Also in this case only an operation could help to remove the lithotriptor and the concrement out of the body of the patient.

It is an object of the present invention to improve a lithotriptor of the above mentioned kind so that a large force can be transferred to the catch basket enabling to decompose hard concrements without the risk of breaking parts of the pull string or the catch strings as well as offering the possibility to detach afterwards the catch basket from extreme hard and therewith indestructible concrements.

According to the invention this is achieved in that the pull string is formed by a wire rope being stranded at least twice, the number of strands of which corresponds to at least the number of catch strings of the catch basket, whereby the catch strings are formed by deformed rope strands of the wire rope which continuously run from the wire rope up to the top of the catch basket.

Due to the use of a twice stranded wire rope made from rope strands stranded in itself which on their part are stranded with each other for forming the wire rope, the pull string has a large ultimate tensile strength having at the same time a uniform distribution of the strength over the rope strands. Due to the provision to form the catch basket from deformed rope strands of the wire rope also their ultimate tensile strength is relatively large. Consequently, the weakest point of the lithotriptor lies at the top of the catch basket because of the subsequent fastening of the free ends of the rope strands by soldering or clamping. Therewith a sort of predetermined breaking point is created here which breaks at an excessive high tensile strain. In such a case the catch basket opens and releases the captured indestructible concrement so that the lithotriptor can be removed out of the body cavity. Due to the provision of the pull string to be a twice stranded wire rope and the catch strings of the catch basket to be rope strands of this wire rope, in case of need very large tensile forces can be transferred to the fastening point of the catch strings at the top of the catch basket so that its strength can be large enough not to open during normal use of the lithotriptor.

According to a preferred embodiment of the invention the rope strands of the wire rope are unstranded and run parallel to each other between a first sleeve surrounding the wire rope and being arranged in a distance to the foot of the catch basket and the foot of the catch basket, where they are held tight by a second sleeve. The number of strands of the wire rope may exceed the number of the catch strings of the catch basket whereby the exceeding number of rope strands may end into the second sleeve. Due to the unstranding of the pull string at its end portion its flexibility is increased there so that the catch basket can be manipulated in an easier way in the body cavity in order to catch the concrement. It has been found especially advantageous if the part section between the sleeves is 3 to 15 cm, preferably 7 to 11 cm.

Advantageously the wire rope has seven rope strands and these nineteen wires respectively.

According to a preferred embodiment of the invention the pull mechanism includes a clamping mechanism for clamping the pull string at its proximal end whereby the clamping mechanism is constructed as a chuck being arranged coaxially to the pull string at the rear end of the pull mechanism, the chuck having at its base a central opening for the pull string. Due to the construction of the pull string as a stranded wire rope it is possible to clamp the pull string by means of a chuck. In contrary hereto the common clamping in a chuck of a plurality of rope strands not being joint with each other and running parallel to each other is not possible because the clamping forces would be distributed on the single rope strands in an undefined manner and consequently a joint clamping of all rope strands cannot be expected.

The chuck can be designed in the kind of an usual drill chuck for instance of a portable drilling machine. It has been proved to be highly satisfactory in designing the clamping mechanism as a chuck that the tensile forces are introduced into the pull string very symmetrically and no considerable weakening or even a damage of the pull string is caused by the clamping forces. Further, it is possible to fasten the pull string at any of its points without buckling so that the use of a correspondingly long pull string together with catheters of different length causes no problems. Further, if the concrement is captured the possibility exists to retract the pull string with still loosened chuck until the concrement is tightly surrounded by the catch strings and only then to clamp the pull string in the chuck. Should the occasion arise the travel of the pull mechanism can be considerable reduced by this measure.

Advantageously the chuck consists of stainless steel and is connected via a metal sleeve to the pull mechanism which is preferably made of plastics. According to a further preferred embodiment of the invention the inner surface of the chuck clamping the pull string is provided with a structure affording a firm grip, e.g. with corrugations.

The pull mechanism preferably has a hollow pull rod which is slidably arranged in a handle, which projects out of the handle, the chuck being fastened to the handle which is provided with an outside thread portion at its portion projecting out of the handle, and an adjusting screw nut being supported at the handle and engaging the outside thread portion, the nut being coupled with a conical pinion being rotatable by means of a conical gear wheel with an operation handle, the gear wheel engaging the conical pinion.

The number of teeth of the conical pinion and the conical gear wheel may by identical. However, the number of teeth of the conical wheel may also be larger than the number of teeth of the conical pinion so that a force multiplication is provided for a good tightening of the adjusting screw nut. For instance, the operation handle may be a crank attached to the conical gear wheel, however it is advantageously designed as a handwheel.

In the following, the invention is explained by the description of a preferred embodiment with reference to the accompanying drawings.

Figure 2:
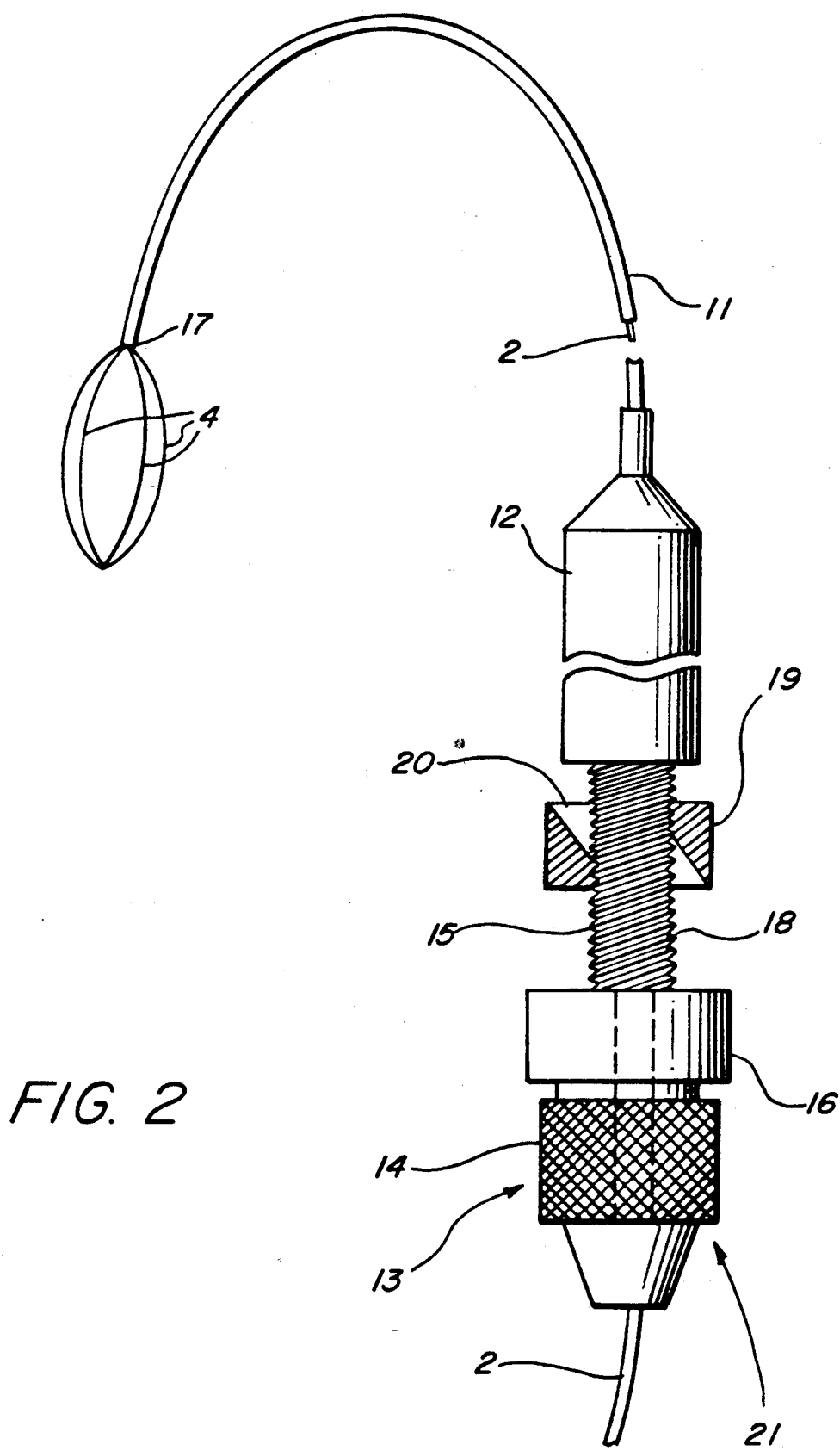
Figure 3:
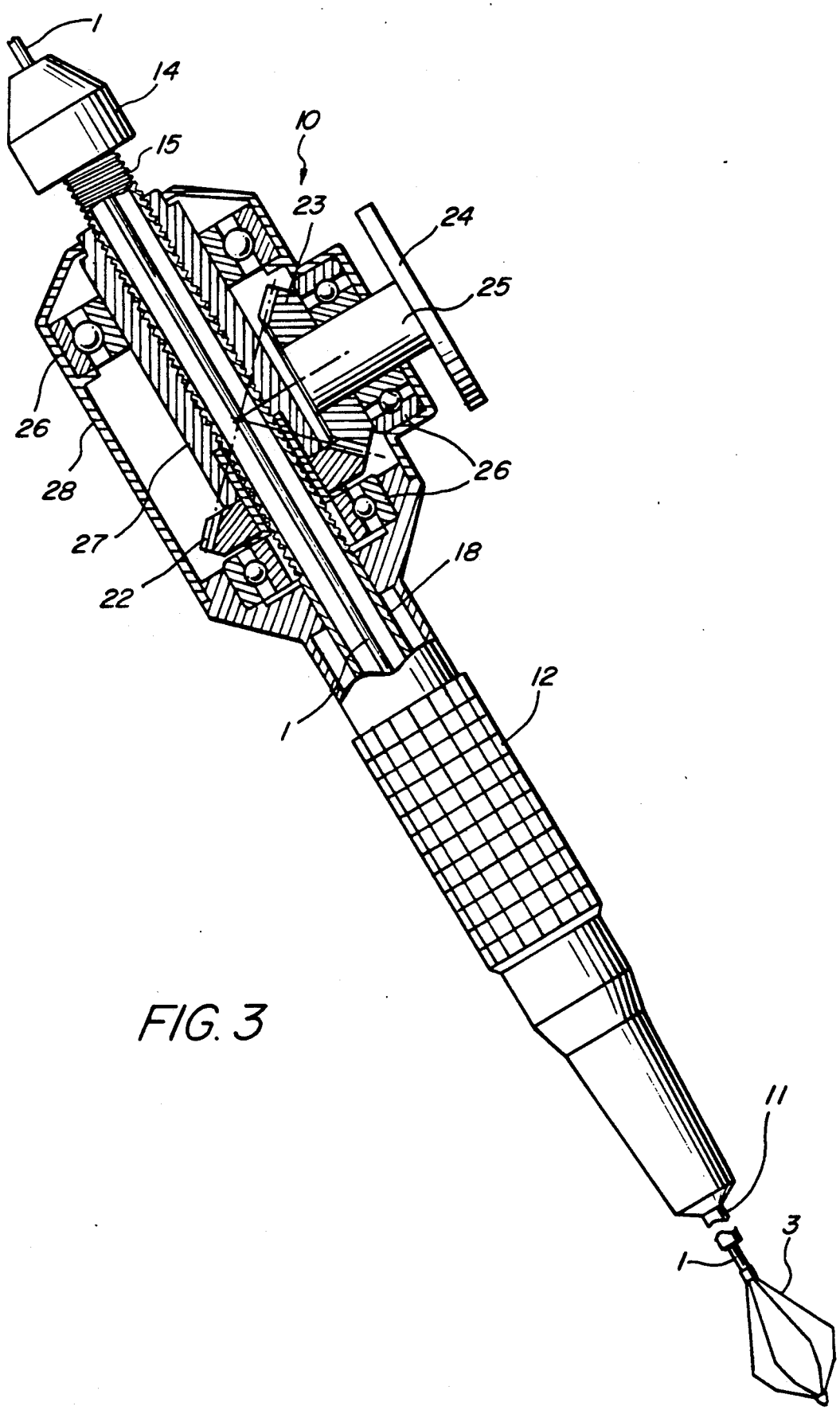

In the drawings show:

FIG. 1: the complete end portion of the pull string and the catch basket of the lithotriptor in a side view;

FIG. 2: a side view of a first preferred embodiment of the lithotriptor as a whole with a chuck and a tilting screw; and FIG. 3: a side view of a second preferred embodiment of the complete lithotriptor with a chuck and a worm gear.

As can be derived from FIG. 1 the pull string 1 of the lithotriptor is designed over a considerable length as a twice stranded wire rope 2. At its distal end the pull string 1 has a catch basket 3 which is formed by at least a portion of the rope strands 4 constituting the wire rope 2. The wire rope 2 runs from the proximal end up to a first sleeve 5 in a twice stranded manner. In the shown embodiment the wire rope 2 comprises seven rope strands 4 stranded in itself which consist of nineteen wires respectively. Behind the first sleeve 5 the wire rope 2 is unstranded which means that the rope strands 4 run parallel to each other up to a second sleeve 6 at the foot of the catch basket. On this unstranded part section 7 between the first sleeve 5 and the second sleeve 6 the rope strands 4 are not biased but straightened so that a supple, flexible part section 7 is formed. The part section 7 is about 3 to 15 cm long, preferably 7 to 11 cm. In dependence on the length of the part section 7 it may be useful to provide one or more guiding sleeves 8 which prevent that the rope strands 4 split up on the part section 7 and that possibly due to this effect the capturing of the concrement is complicated.

The first sleeve 5 serves to prevent a further unstranding of the wire rope 2 in direction to its proximal end. For this reason as well, the first sleeve 5 and the second sleeve 6 shall comprise attachment means which guarantee a fixing of the rope strands 4. This can be achieved by clamping, by soldering, by bonding as well as by other suitable fixing means. Behind the second sleeve 6 only those rope strands 4 are carried on which serve to form the catch basket 3. In the embodiment there are five rope strands 4 which are outwardly convex curved behind the wire rope 2 running unstranded. The rope strands 4 forming the catch basket 3 are attached to each other at their free ends. In the shown embodiment this is done by soldering the ends in a conical sleeve 9 which forms the top of the catch basket 3. Attention has to be paid that the strength of the joint of the free ends of the strands with each other and with the conical sleeve 9 is smaller than the admissible ultimate tensile stress.

In principal all rope strands 4 except the core of the wire rope 2 can be used for the formation of the catch basket 3. The core of the wire rope 2 ends either at the first sleeve 5 or at the second sleeve 6. All other rope strands 4 not used for the formation of the catch basket 3 end at the second sleeve 6 where they are preferably soldered.

FIG. 2 shows a side view of a preferred embodiment of the lithotriptor as a whole including a pull mechanism 10 for introducing and retracting the catch basket 3 out of a casing 11 which surrounds the pull string in a Bowden cable like guiding manner. This flexible casing 11 consists, for instance, of a flexible tube made of a helically wound steel wire. The tube is supported at a handle 12 and the pull string 1 runs through it. The catch basket 3 is arranged at the distal end of the pull string 1. The proximal end of the pull string 1 is fixed in a hollow pull rod 15 by means of a clamping mechanism 13 which mainly consists of a chuck 14. The pull rod 15 is in an axial direction slidably arranged within the handle 12. A metal sleeve 16 is provided as an intersection piece between the pull rod 15 which advantageously consists of a synthetic material and the clamping mechanism 13 which preferably consists of a stainless steel, like for instance V2A. By sliding the pull rod 15 into the handle 12 the catch basket 3 is driven out of the distal end of the casing 11 by the pull string 1 whereas the catch basket 3 is driven back into the distal end 17 of the catheter by pulling the pull rod 15 out of the handle 12.

An outside thread 18 with a small pitch is provided on the pull rod 15 so that a threaded rod is formed. An adjusting screw nut 19 is screwable on the threaded rod. In accordance with this embodiment the adjusting screw nut 19 is constructed as a quick slidable nut, which can be disengaged from the outside thread 18 by tilting or canting the nut 19 with its inside thread away from the pull rod 15. In this canted position the screw nut 19 can be freely slided in axial direction. For this purpose the adjusting screw nut 19 has a sloping boring 2o which runs oblique to the thread boring. The diameter of the sloping boring is chosen slightly larger than the outer diameter of the outside thread 18 of the threaded or pull rod 15 for achieving a clearance and a thereby caused easy movability of the adjusting screw nut 19 after being canted.

The clamping chuck 14 is arranged via the metal sleeve 16 at the free end of the pull rod 15. The bottom or base of the chuck 14 has a continuous central opening 21 through which the pull string 1 is led out of the hollow pull rod 15. The clamping mechanism 13 is arranged in such a way that the opening 21 is aligned with the longitudinal axis of the hollow pull rod 15.

The chuck 14 can be designed as a three cheek chuck like a conventional drill chuck of an electric portable drilling machine. However the displacing toothed ring for opening and closing the chuck by means of a key does not need to be provided since a manual operation of the chuck is normally sufficient in the present case.

FIG. 3 shows a partly cut longitudinal view of a second preferred embodiment of a complete lithotriptor. In contrast to the first preferred embodiment shown in FIG. 2 the adjusting screw nut 27 of the pull mechanism 10 is not turned by manipulating with the hand for retracting the catch basket but is turned by an angular gear by means of a handwheel 24. The angular gear consists of a conical pinion 22 which coaxially surrounds the hollow pull rod 15 and which is firmly coupled to the adjusting screw nut 27 and of a toothed conical wheel 23 which engages with the conical pinion 22. The handwheel is firmly fixed to the conical toothed wheel 23 by a shaft 25 which is common to the handwheel 24 and the conical toothed wheel 23. The sleevelike adjusting screw nut 27, the conical pinion 22 as well as the conical toothed wheel 23 with the handwheel 24 are born in bearings 26 within a housing 28 attached to the handle 12.

The embodiment of FIG. 3 functions as follows: rod 15 is hollow in order to receive pull spring 1, which is fixedly clamped in chuck 14. Rod 15 is slidably received in handle 12 and is provided with an outer thread 18. Adjusting screw nut 27 is provided with an inner thread engaging the outer thread 18 of rod 15 and is axially supported via the lower bearing 26 at handle 12. Now, if the hand wheel 24 is rotated, the toothed wheel 23, conical pinion 22 and screw nut 27 are rotated, resulting in axially displacing the pull rod 15 by virtue of the engaging threads and the axial support of nut 27 against handle 12, thereby resulting in displacement of pull string 1.

Nut 19 (FIG. 2) has the same function as nut 27: if nut 19 is (manually) screwed up until it abuts against handle 12, a further rotation of nut 19 results in a displacement of rod 15 and pull string 2.

I claim:

1. A lithotriptor comprising:
a catch basket formed by a plurality of outwardly curved catch strings and having a catch basket foot and a catch basket top and respective joints fixing the catch strings to each other at said catch basket foot and said catch basket top;
a pull string connected to the catch basket strings at the catch basket foot, said pull string comprising a plurality of pull wires;
a casing means for slidably mounting the pull string;
means connected to said pull string for extending and retracting the catch basket, wherein the pull string comprises a wire rope having a plurality of strands twisted together to form said wire rope, each of said strands comprising a plurality of wires twisted together, the number of strands of said wire rope corresponding to at least the number of catch strings of the catch basket, whereby the catch strings are formed by deformed rope strands of the wire rope running continuously from the wire rope to the top of the catch basket, wherein the rope strands of the wire rope are unwound and run parallel to each other along a section between a first sleeve receiving the wire rope and a second sleeve receiving the joint at the foot of the catch basket.

2. The lithotriptor according to claim 1, wherein the number of strands of the wire rope exceeds the number of the catch strings of the catch basket, the exceeding number of rope strands being received by and terminating at the second sleeve.

3. The lithotriptor according to claim 1, wherein the section between the sleeves has a length of 3 to 15 cm.

4. The lithotriptor according to claim 1, wherein the wire rope consists of seven rope strands and each of these rope strands consists of nineteen wires.

5. The lithotriptor according to claim 1, wherein the means for extending and retracting has a base and a rear end and further includes a clamping means for clamping the pull string at its proximal end wherein the clamping means comprises a chuck arranged coaxially to the pull string at the rear end of the means for extending and retracting, the chuck having at its base a central opening for the pull string.

6. A lithotriptor according to claim 5, wherein the chuck consists of stainless steel and further includes a metal sleeve connecting the chuck to the means for extending and retracting.

7. A lithotriptor according to claim 5, wherein the chuck has an inner surface including corrugation means for releasably clamping the pull string.

8. The lithotriptor of claim 1 wherein the joint fixing the catch strings at the catch basket top has a strength which is smaller than the strength of each of the catch strings, thereby forming a breaking point for breaking open said catch basket in response to excessive force.

9. A lithotriptor comprising:
a catch basket formed by a plurality of outwardly curved catch strings and having a catch basket foot and a catch basket top and respective joints fixing the catch strings to each other at said catch basket foot and said catch basket top;
a pull string connected to the catch basket strings at the catch basket foot, said pull string comprising a plurality of pull wires;
a casing means for slidably mounting the pull string;
means connected to said pull string for extending and retracting the catch basket, wherein the pull string comprises a wire rope having a plurality of strands twisted together to form said wire rope, each of said strands comprising a plurality of wires twisted together, the number of strands of said wire rope corresponding to at least the number of catch strings of the catch basket, whereby the catch strings are formed by deformed rope strands of the wire rope running continuously from the wire rope to the top of the catch basket, wherein the means for extending and retracting has a base and a rear end and further includes a clamping means for clamping the pull string at its proximal end, wherein the clamping means comprises a chuck arranged coaxially to the pull string at the rear end of the means for extending and retracting the chuck having at its base a central opening for the pull string, wherein the means for extending and retracting includes a hollow pull rod slidably arranged in a handle and projecting out of the handle, said pull string passing through said hollow pull rod and through said central opening into the chuck, the chuck being secured to the pull rod, said pull rod having an outside thread section at the portion thereof projecting out of the handle, and an adjusting screw nut supported at the handle and engaging the outside thread portion of the screw nut; and further comprising:
a conical pinion rotatably coupled to said screw nut;
a conical gear wheel rotatingly engaging the conical pinion; and
an operation handle means for rotating the conical gear wheel, thereby rotating said conical pinion, thereby adjusting said screw nut, thereby slidingly displacing the pull rod and the pull string with respect to the handle.

10. Lithotriptor according to claim 9, wherein the operation handle is an handwheel.

11. A lithotriptor comprising:
a catch basket formed by a plurality of outwardly curved catch strings and having a catch basket foot and a catch basket top and respective joints fixing the catch strings to each other at said catch basket foot and said catch basket top;
a pull string connected to the catch basket strings at the catch basket foot, said pull string comprising a plurality of pull wires;
a casing means for slidably mounting the pull string;
means connected to said pull string for extending and retracting the catch basket, wherein the pull string comprises a wire rope having a plurality of strands twisted together to form said wire rope, each of said strands comprising a plurality of wires twisted together, the number of strands of said wire rope corresponding to at least the number of catch strings of the catch basket, whereby the catch strings are formed by deformed rope strands of the wire rope running continuously from the wire rope to the top of the catch basket, wherein the rope strands of the wire rope are unwound and run parallel to each other along a section between a first fixing point fixing the rope strands together and a second fixing point fixing the rope strands together at the joint at the foot of the catch basket.

12. The lithotriptor of claim 11, wherein said rope strands are fixed together by soldering at said first and second fixing points.

* * * * *